US007195873B2

(12) United States Patent
Filigheddu et al.

(10) Patent No.: US 7,195,873 B2
(45) Date of Patent: Mar. 27, 2007

(54) DRUG RESPONSE MARKER IN BETA-1 ADRENERGIC RECEPTOR GENE

(75) Inventors: Fabiana Filigheddu, Sassari (IT); Julia Reid, Salt Lake City, UT (US); Susanne Wagner, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 513 days.

(21) Appl. No.: 10/331,192

(22) Filed: Dec. 27, 2002

(65) Prior Publication Data

US 2003/0143608 A1 Jul. 31, 2003

Related U.S. Application Data

(60) Provisional application No. 60/344,083, filed on Dec. 27, 2001.

(51) Int. Cl.
C12Q 1/68 (2006.01)
(52) U.S. Cl. ......................................................... 435/6
(58) Field of Classification Search ...................... None
See application file for complete search history.

(56) References Cited

U.S. PATENT DOCUMENTS

| 6,043,031 | A  | * | 3/2000  | Koster et al. ................. | 435/6 |
| 6,498,009 | B1 |   | 12/2002 | Liggett |  |
| 2002/0187491 | A1 |   | 12/2002 | Johnson |  |
| 2005/0181386 | A1 | * | 8/2005  | Diamond et al. .............. | 435/6 |

FOREIGN PATENT DOCUMENTS

WO     WO 99/19512     4/1999

OTHER PUBLICATIONS

Ferrari et al. "Genetic mapping and tailored antihypertensive therapy", Cardiovascular Drugs and Therapy, vol. 14, No. 4, pp. 387-395, 2000.*
White et al. "Update on the drug treatment of hypertension in patients with cardiovascular disease", The American Journal of Medicine, vol. 118, pp. 695-705, 2005.*
Mellen et al. "Pharmacogenomics of blood pressure response to antihypertensive treatment", Journal of Hypertension, vol. 23, pp. 1311-1325, 2005.*
Karlsson et al. Beta-1 adrenergic receptor gene polymorphisms and response to beta-1 adrenergic receptor blockade in patients with essential hypertension, Clinical Cardiology, vol. 27, No. 6, Suppl. 3, pp. 347-350, 2004.*
Filigheddu et al. "Genetic polymorphisms of the beta-adrenergic system: association with essential hypertension and response to beta-blockade", The Pharmacogenomics Journal, vol. 4, pp. 154-160, 2004.*
Johnson et al. "Beta-1 adrenergic receptor polymorphisms and antihypertensive response to metoprolol", Clinical Pharmacology & Therapeutics, vol. 74, pp. 44-52, 2003.*

Brain et al. "Pharmacogenomics in hypertension: present practicalities and future potential", Journal of Hypertension, vol. 23, pp. 1327-1329, 2005.*
Liljedahl et al. "A microarray minisequencing system for pharmacogenetic profiling of antihypertensive drug response", Pharmacogenetics, vol. 13, pp. 7-17, 2003.*
Filigheddu et al. "Genetic polymorphisms of the beta-adrenergic receptor system are not associated with essential hypertension and do not predict the effect of beta-blockers in a north Sardinian cohort", J. Hypertension, vol. 20, Supp.[4], p. S19, 2002.*
Leineweber "Beta-adrenergic receptor polymorphism in human cardiovascular disease", Annals of Medicine, vol. 36, Suppl. 1, pp. 64-69, 2004.*
Lizardi et al. "Mutation detection and single-molecule counting using isothermal rolling-circle amplification", Nature genetics, vol. 19, pp. 225-232, 1998.*
Hessner et al. "Genotyping of Factor V G1691A (Leiden) without the use of PCR by invasive cleavage of oligonucleotide probes", Clinical Chemistry, vol. 46, No. 8, pp. 1051-1056, 2000.*
Wikipedia entry entitled "Thiazide" from Wikipedia, the free encyclopedia, accessed May 30, 2006 at http://en.wikipedia.org/wiki/Thiazide, 2 pages.*
Piazza, Alberto, "Who Are the Europeans?", *Science*, Jun. 18, 1993; 260:1767-1769.
Hingorani, Aroon D., et al., "Renin-angiotensin system gene polymorphisms influence blood pressure and the response to angiotensin converting enzyme inhibition", *Journal of Hypertension*, 1995; 13:1602-1609.
Haiyan, Jia, et al., "Association of the $G_s\alpha$ Gene With Essential Hypertension and Response to β-Blockade", *Hypertension*, 1999; 34:8-14.
Glorioso, Nicola, et al., "The Role of α-Adducin Polymorphism in Blood Pressure and Sodium Handling Regulation May Not Be Excluded by a Negative Association Study", *Hypertension*, 1999; 34:649-654.
Borjesson, M., et al., "A novel polymorphism in the gene coding for the $beta_1$-adrenergic receptor associated with survival in patients with heart failure", *European Heart Journal*, 2000; 21:1853-1858.
Podlowski, Svenia, et al., "$β_1$-Adrenoceptor gene variations: a role in idiopathic dilated cardiomyopathy?", *J. Mol. Med.*, 2000; 78:87-93.

(Continued)

*Primary Examiner*—Juliet C. Switzer
(74) *Attorney, Agent, or Firm*—Jay Z. Zhang; Myriad Genetics IP Dept.

(57) ABSTRACT

Methods of using a genetic polymorphic variation in the human beta-1 adrenergic receptor gene as a drug response marker are presented. Determining the presence or absence of the A145G genetic variation in the human beta-1 adrenergic receptor gene is useful in predicting an individual's relative response to different antihypertensive drugs; optimizing antihypertensive treatment for an individual; selecting candidate human subjects for participation in clinical trials involving antihypertensive drugs; and, predicting the relative responses among a plurality of individuals to an antihypertensive drug.

12 Claims, No Drawings

OTHER PUBLICATIONS

Samani, N.J., "Pharmacogenomics of hypertension: a realizable goal?", *Clinical Science*, 2000; 99:231-232.
Wolf, C Roland, et al., "Science, medicine, and the future—Pharmacogenetics", *BMJ*, Apr. 8, 2000; 320:987-990.
Drysdale, Connie M., et al., "Complex promoter and coding region $\beta_2$ - adrenergic receptor haplotypes alter receptor expression and predict *in vivo* responsiveness", *PNAS*, Sep. 12, 2000; 97(19):10483-10488.
Turner, Stephen T., et al., "Antihypertensive pharmacogenetics: getting the right drug into the right patient", *Journal of Hypertension*, 2001; 19:1-11.
Bengtsson, Kristina, et al., "Polymorphism in the $\beta_1$-Adrenergic Receptor Gene and Hypertension", *Circulation*, 2001; 104:187-190.
Ranade, Koustubh, et al., "A Polymorphism in the β1 Adrenergic Receptor Is Associated with Resting Heart Rate", *Am. J. Hum. Genet.*, 2002; 70:935-942α.

* cited by examiner

SEQUENCE LISTING

<160> NUMBER OF SEQ ID NOS: 2

<210> SEQ ID NO 1
<211> LENGTH: 1723
<212> TYPE: DNA
<213> ORGANISM: Homo sapiens

<400> SEQUENCE: 1

```
tgctacccgc gcccgggctt ctggggtgtt ccccaaccac ggcccagccc tgccacaccc      60 cccgccccg gcctccgcag ctcggcatgg gcgcgggggt gctcgtcctg ggcgcctccg     120
agcccggtaa cctgtcgtcg gccgcaccgc tccccgacgg cgcggccacc gcggcgcggc     180
tgctggtgcc cgcgtcgccg cccgcctcgt tgctgcctcc cgccagcgaa agccccgagc     240
cgctgtctca gcagtggaca gcgggcatgg gtctgctgat ggcgctcatc gtgctgctca     300
tcgtggcggg caatgtgctg gtgatcgtgg ccatcgccaa gacgccgcgg ctgcagacgc     360
tcaccaacct cttcatcatg tccctggcca gcgccgacct ggtcatgggg ctgctggtgg     420
tgccgttcgg ggccaccatc gtggtgtggg gccgctggga gtacggctcc ttcttctgcg     480
agctgtggac ctcagtggac gtgctgtgcg tgacggccag catcgagacc ctgtgtgtca     540
ttgccctgga ccgctacctc gccatcacct cgcccttccg ctaccagagc ctgctgacgc     600
gcgcgcgggc gcggggcctc gtgtgcaccg tgtgggccat ctcggccctg gtgtccttcc     660
tgcccatcct catgcactgg tggcgggcgg agagcgacga ggcgcgccgc tgctacaacg     720
accccaagtg ctgcgacttc gtcaccaacc gggcctacgc catcgcctcg tccgtagtct     780
ccttctacgt gcccctgtgc atcatggcct tcgtgtacct gcgggtgttc cgcgaggccc     840
agaagcaggt gaagaagatc gacagctgcg agcgccgttt cctcggcggc cagcgcggc     900 cgccctcgcc ctcgccctcg cccgtccccg cgcccgcgcc gccgccgga ccccgcgcc     960 ccgccgccgc cgccgccacc gccccgctgg ccaacgggcg tgcgggtaag cggcggccct    1020
cgcgcctcgt ggccctacgc gagcagaagg cgctcaagac gctgggcatc atcatgggcg    1080
tcttcacgct ctgctggctg cccttcttcc tggccaacgt ggtgaaggcc ttccaccgcg    1140
agctggtgcc cgaccgcctc ttcgtcttct caactggct gggctacgcc aactcggcct    1200
tcaaccccat catctactgc cgcagcccg acttccgcaa ggccttccag ggactgctct    1260
gctgcgcgcg cagggctgcc cgccggcgcc acgcgaccca cggagaccgg ccgcgcgcct    1320
```

-continued

```
cgggctgtct ggcccggccc ggaccccgc catcgcccgg ggccgcctcg gacgacgacg    1380
acgacgatgt cgtcggggcc acgccgcccg cgcgcctgct ggagccctgg gccggctgca    1440
acggcggggc ggcggcggac agcgactcga gcctggacga gccgtgccgc cccggcttcg    1500
cctcggaatc caaggtgtag ggcccggcgc ggggcgcgga ctccgggcac ggcttcccag    1560
gggaacgagg agatctgtgt ttacttaaga ccgatagcag gtgaactcga agcccacaat    1620
cctcgtctga atcatccgag gcaaagagaa aagccacgga ccgttgcaca aaaaggaaag    1680
tttgggaagg gatgggagag tggcttgctg atgttccttg ttg                      1723

<210> SEQ ID NO 2
<211> LENGTH: 208
<212> TYPE: RNA
<213> ORGANISM: Homo sapiens

<400> SEQUENCE: 2
gagcccggua accgucguc ggccgcaccg cuccccgacg gcgcggccac cgcggcgcgg       60 cugcugguge ccgcgucgcc gcccgccucg uugcugccuc ccgccagcga argccccgag     120
ccgcugucuc agcaguggac agcgggcaug ggucugcuga uggcgcucau cgugcugcuc    180
aucguggcgg gcaaugugcu ggugaucg                                        208
```

DRUG RESPONSE MARKER IN BETA-1 ADRENERGIC RECEPTOR GENE

RELATED US APPLICATIONS

This application claims the benefit (under 35 U.S.C. §119(e)) of U.S. Provisional Application No. 60/344,083 filed on Dec. 27, 2001, which is incorporated herein by reference in its entirety.

FIELD OF THE INVENTION

This invention relates to pharmacogenetics, particularly to the use of a genetic polymorphic variation in the human beta-1 adrenergic receptor gene.

BACKGROUND OF THE INVENTION

Hypertension (elevated blood pressure) is a common health problem and often a devastating disease. In addition to being one of the most important risk factors in both coronary heart disease and cerebrovascular accidents, hypertension may also lead to cardiac hypertrophy with heart failure, aortic dissection, and renal failure. Although several drugs have been developed to reverse the harmful effects of hypertension, and to lower blood pressure in patients, the pharmacology of hypertension remains poorly understood. Furthermore, a wide variety of drug classes targeting different biochemical pathways thought to be involved in hypertension further complicate the ability of physicians to match the right drug with the right patient. For example, individual patients often vary widely in their response to different types of antihypertensive drugs. See Samani, *Clinical Science*, 99:231–232 (2000). One illustration of this is the poor response of black patients to a class of drugs known as angiotensin converting enzyme (ACE) inhibitors compared with that of Caucasians. Additionally, even individual responses to antihypertensive drugs within a relatively homogenous group vary a great deal. See Dickerson et al., *Lancet*, 353:2008–2013 (1999).

At present, clinical and/or biochemical parameters providing a useful guide to how well a hypertensive patient will respond to drug treatment are non-existent. Thus, patients are either left with inadequate treatment, or are rotated through different classes of antihypertensive drugs, both of which come at a great cost in terms of individual health, and health care. See Dickerson et al., *Lancet*, 353:2008–2013 (1999); Samani, *Clinical Science*, 99:231–232 (2000).

Therefore, it would be desirable to provide simple and effective methods for determining the most effective drug for a particular patient among the various different classes of antihypertensive drugs.

SUMMARY OF THE INVENTION

The present invention is based on the discovery that a genetic variant in the human beta-1 adrenergic receptor gene is significantly associated with an individual's response to antihypertensive drugs. The genetic variant according to the present invention is the A145G nucleotide substitution mutation, which has been shown to be associated with an individual's response to antihypertensive drugs. Specifically, it has been discovered that an individual homozygous for the A145G genetic variant responds more favorably to a diuretic antihypertensive class of drugs than to angiotensin converting enzyme inhibitors and beta-blockers. Thus, the present invention provides a genetic basis for predicting an individual's response to antihypertensive drugs.

Accordingly, the present invention provides methods for predicting the relative responses of an individual to different classes of antihypertensive drugs by determining the presence or absence of the A145G nucleotide substitution variant in the beta-1 adrenergic receptor gene in the individual, wherein if the individual is homozygous for this genetic variant, the individual will respond more effectively to diuretic antihypertensive drugs (e.g., hydrochlorothiazide) than to angiotensin converting enzyme inhibitors (e.g., fosinopril) and beta-blockers (e.g., atenolol).

The methods of the present invention are useful in optimizing antihypertensive treatment of patients and in optimizing clinical trials involving antihypertensive drug treatment.

The foregoing and other advantages and features of the invention, and the manner in which the same are accomplished, will become more readily apparent upon consideration of the following detailed description of the invention taken in conjunction with the accompanying examples, which illustrate exemplary embodiments.

DETAILED DESCRIPTION OF THE INVENTION

The terms "genetic variant," "mutation," "nucleotide variant," and "nucleotide substitution" are used herein interchangeably to refer to nucleotide changes in a reference nucleotide sequence of a particular gene.

The term "genotype" as used herein means the nucleotide characters at a particular nucleotide variant marker (or locus) in either one allele or both alleles of a gene (or a particular chromosome region). With respect to the nucleotide 145 position of beta-1 adrenergic receptor gene, the nucleotide(s) at that locus or equivalent thereof in one or both alleles form the genotype of the beta-1 adrenergic receptor gene at that locus. A genotype can be homozygous or heterozygous. Accordingly, "genotyping" means determining the genotype, that is, the nucleotide(s) at a particular gene locus.

The phrase "the nucleotide 145 position of beta-1 adrenergic receptor gene" means the locus at nucleotide position +145 of a beta-1 adrenergic receptor cDNA or mRNA with the sequence shown in SEQ ID NO: 1 as a reference sequence for alignment, wherein the A of the ATG (or AUG) of the initiation Met codon is nucleotide +1. It also encompasses the corresponding locus in a beta-1 adrenergic receptor genomic DNA. SEQ ID NO:2 shows a portion of the nucleotide sequence of beta-1 adrenergic receptor mRNA. The A145G genetic variant of the present invention is identified in the sequence by the symbol "R," in the sequence of SEQ ID NO:2.

As used herein, the terms "amino acid variant," "amino acid mutation," and "amino acid substitution" are used herein interchangeably to refer to amino acid changes to a reference protein sequence resulting from a genetic variant or a mutation to the reference gene sequence encoding the reference protein.

The term, "reference sequence" refers to a polynucleotide or polypeptide sequence known in the art, including those disclosed in publicly accessible databases, e.g., GenBank, or a newly identified gene or protein sequence, used simply as a reference with respect to the genetic variant or amino acid variant provided in the present invention.

The term "allele" or "gene allele" is used herein to refer generally to a gene having a reference sequence or a gene containing a specific genetic variant.

The term "locus" refers to a specific position or site in a gene sequence or protein sequence. Thus, there may be one or more contiguous nucleotides in a particular gene locus, or one or more amino acids at a particular locus in a polypeptide. Moreover, "locus" may also be used to refer to a particular position in a gene sequence where one or more nucleotides have been deleted, inserted, or inverted.

As used herein, the terms "polypeptide," "protein," and "peptide" are used interchangeably to refer to amino acid chains in which the amino acid residues are linked by covalent peptide bonds. The amino acid chains can be of any length of at least two amino acids, including full-length proteins. Unless otherwise specified, the terms "polypeptide," "protein," and "peptide" also encompass various modified forms thereof, including but not limited to glycosylated forms, phosphorylated forms, etc.

The terms "primer," "probe," and "oligonucleotide" may be used herein interchangeably to refer to a relatively short nucleic acid fragment or sequence. They can be DNA, RNA, or a hybrid thereof, or a chemically modified analog or derivatives thereof. Typically, they are single stranded. However, they can also be double-stranded having two complementing strands which can be separated apart by denaturation. Normally, they have a length of from about 8 nucleotides, and more preferably about 18 to about 50 nucleotides. They can be labeled with detectable markers or modified in any conventional manners for various molecular biological applications.

The terms "hypertension" and "hypertensive" used herein refer to symptoms related to undesirably high levels of blood pressure. Individuals said to have "symptoms related to hypertension" have blood pressure levels at an undesirably high level. For example, an individual with a diastolic blood pressure above 89 mmHg and a systolic blood pressure above 139 mmHg, is considered to have an undesirably high level of blood pressure by the medical community.

"Antihypertensive" treatment and "treating hypertension" as used herein refer to treatment intended to reduce diastolic and/or systolic blood pressure from an undesirably high level (i.e., a level that is considered a disease or disorder under conventional medical standards, or a level that is desired to be reduced for any reason). Individuals with only temporary periods of hypertension—wherein their blood pressure levels only temporarily exceed levels which become undesirable, but then fall to more desirable levels—may also be deemed as having symptoms related to hypertension. Patients with primary, essential, idiopathic hypertension, and secondary hypertension (e.g., renal hypertension and endocrine hypertension) are included in the category of individuals with hypertension.

The terms "diuretic" and "diuretic antihypertensive" are used herein to refer to drugs that affect sodium diuresis and volume depletion in a patient. Thus, diuretic antihypertensives include thiazides (such as hydrochlorothiazide, chlorothiazide, and chlorthalidone), metolazone, loop diuretics (such as furosemide, bumetanide, ethacrynic acid, piretanide and torsemide), and aldosterone antagonists (such as spironolactone, triamterene, and amiloride).

The terms "beta blocker" and "beta blocker antihypertensive" are used herein to refer to beta-adrenergic receptor blocking agents, i.e., drugs that block sympathetic effects on the heart and are generally most effective in reducing cardiac output and in lowering arterial pressure when there is increased cardiac sympathetic nerve activity. In addition, these drugs block the adrenergic nerve-mediated release of rennin from the renal justaglomerular cells. Examples of this group of drugs include, but are not limited to, chemical agents such as propranolol, metoprolol, nadolol, atenolol, timolol, betaxolol, carteolol, pindolol, acebutolol, labetalol, and carvediol.

The terms "angiotensin converting enzyme inhibitor," and "angiotensin converting enzyme inhibitor antihypertensive" are used herein to refer to drugs that are commonly known as ACE inhibitors. This group of drugs includes, for example, chemical agents such as captopril, benazepril, enalapril, enalaprilat, fosinopril, lisinopril, quinapril, ramipril, and trandolapril.

A cDNA sequence of the beta-1 adrenergic receptor gene is disclosed under GenBank Accession No. J03019. This sequence is used herein as a reference sequence for identifying the polymorphic position of the A145G genetic variant of the present invention. The A145G genetic variant is located at nucleotide position +145 of the beta-1 adrenergic receptor gene mRNA, or cDNA, wherein the A of the ATG of the initiation Met codon is nucleotide +1. The amino acid variant Ser49Gly referred to herein is at position +49 of the protein product of the beta-1 adrenergic receptor mRNA or cDNA, wherein the initiation Met amino acid is amino acid +1.

Thus, in accordance with the present invention, the A145G genetic variant of the human beta-1 adrenergic receptor gene is now, according to the present invention, shown to affect individual response to antihypertensive drug treatment in patients. That is, individuals homozygous for the A145G genetic variant, respond more effectively to antihypertensive drug treatment using diuretic antihypertensive drugs (e.g., hydrochlorothiazide), than to either angiotensin converting enzyme inhibitors (e.g., fosinopril) or beta blockers (e.g., atenolol).

The A145G genetic variant results in the substitution of a non-hydroxyl amino acid for the hydroxy group-containing amino acid Ser49. Thus, an individual lacking a beta-1 adrenergic receptor that has a hydroxy group-containing amino acid (e.g., Ser49 or Thr49) would likely also respond more favorably to antihypertensive drug treatment using diuretic antihypertensive drugs (e.g., hydrochlorothiazide), than to either angiotensin converting enzyme inhibitors (e.g., fosinopril) or beta blockers (e.g., atenolol). Thus, other nucleotide variants at the nucleotide position 145, 146 and 147 of beta-1 adrenergic receptor gene leading to the substitution of a non-hydroxyl amino acid for the hydroxy group-containing amino acid Ser49 should also cause similar effect as A145G.

Accordingly, in one aspect, the present invention provides methods for selecting an antihypertensive treatment for an individual, which include the steps of identifying an individual in need of an antihypertensive treatment, and determining the presence or absence of an A145G nucleotide variant or a nucleotide variant resulting in a Ser49Gly amino acid substitution in a nucleic acid of the individual encoding beta-1 adrenergic receptor, or the presence or absence of a Ser49Gly amino acid variant in the beta-1 adrenergic receptor protein of the individual.

In one embodiment, the methods for selecting an antihypertensive treatment for an individual comprise identifying an individual in need of an antihypertensive treatment, and determining the genotype of the individual at the nucleotide 145 position of the beta-1 adrenergic receptor gene.

In another embodiment, the methods for selecting an antihypertensive treatment for an individual comprise determining the genotype of the individual at the nucleotide 145 position of the beta-1 adrenergic receptor gene, wherein the presence of a homozygous A145G genetic variant would indicate an increased likelihood that said individual will respond more favorably to diuretic antihypertensive drugs than to angiotensin converting enzyme inhibitors and beta-blockers. Preferably, the diuretic antihypertensive drugs are thiazides (e.g., hydrochlorothiazide), the angiotensin converting enzyme inhibitor is fosinopril, and beta-blocker is atenolol. The genotype can be determined by analyzing nucleic acids isolated from said individual.

In another aspect, the present invention provides methods for predicting an individual's relative response to different classes of antihypertensive drugs by determining or detecting in the individual the presence or absence of a homozygous nucleotide variant of A145G or determining whether an individual has nucleotide variant(s) that make the individual devoid of a beta-1 adrenergic receptor that has a hydroxy group-containing amino acid (e.g., Ser49 or Thr49). The presence of such homozygous mutation or such other nucleotide variant(s) would indicate that there is an increased likelihood that said individual would be more responsive to diuretic antihypertensives than to angiotensin converting enzyme inhibitors and beta-blockers.

Thus, in one embodiment, the methods for predicting the relative response of an individual to different classes of antihypertensive drugs include a step of determining, in an individual with hypertension, the presence or absence of an A145G nucleotide variant or a nucleotide variant resulting in a Ser49Gly amino acid substitution in a nucleic acid of the individual encoding beta-1 adrenergic receptor, or the presence or absence of a Ser49Gly amino acid variant in the beta-1 adrenergic receptor protein of the individual. The determination can be accomplished by genotyping the individual with hypertension to determine the genotype at the nucleotide 145 position of the beta-1 adrenergic receptor gene. The presence of a homozygous A145G genetic variant or a homozygous genetic variant resulting in the Ser49Gly amino acid variant would indicate an increased likelihood that said individual will respond favorably to diuretics than to angiotensin converting enzyme inhibitors and beta-blockers. In particular, the presence of a homozygous A145G genetic variant or a homozygous genetic variant resulting in the Ser49Gly amino acid variant would indicate an increased likelihood that said individual will respond more favorably to hydrochlorothiazide than to fosinopril and atenolol.

In yet another aspect of the present invention, a method is provided for selecting candidate human subjects for participation in a clinical trial involving an antihypertensive drug. The method comprises determining the genotype of an individual at the nucleotide 145 position of the beta-1 adrenergic receptor gene, and deciding whether to include said individual in the clinical trial based on the result of the determining step. Thus, in one embodiment, the method includes determining the presence or absence of a homozygous mutation of A145G in a candidate human subject. The presence of such homozygous mutation would indicate that there is an increased likelihood that said candidate human subject would be more responsive to diuretic antihypertensives than to angiotensin converting enzyme inhibitors and beta-blockers. In a second embodiment, the candidate human subject is tested for a Ser49Gly amino acid substitution in the human beta-1 adrenergic receptor protein, or nucleotide variant(s) that make the individual devoid of a beta-1 adrenergic receptor that has a hydroxy group-containing amino acid (e.g., Ser49 or Thr49). The presence of a homozygous Ser49Gly amino acid substitution or the other nucleotide variant(s) would indicate that there is an increased likelihood that said candidate human subject would be more responsive to diuretic antihypertensives than to angiotensin converting enzyme inhibitors and beta-blockers.

In a further aspect, a method for optimizing antihypertensive treatment in an individual is also provided. Optimizing antihypertensive treatment in an individual involves deciding which class of antihypertensive drug to use or the amount of such drug to administer based on the presence or absence of the A145G genetic variant or the Ser49Gly amino acid variant of the beta-1 adrenergic receptor in that individual. The homozygous presence of either the nucleotide (A145G) or amino acid (Ser49Gly) variant in a particular individual would indicate that there is an increased likelihood that individual would be more responsive to diuretic antihypertensives than to angiotensin converting enzyme inhibitors and beta-blockers. With that information in mind, a particular antihypertensive drug and/or dosage thereof may be selected to better suit a particular individual.

In yet another aspect of the present invention, a method is also provided for treating hypertension in an individual. The method includes (a) predicting an individual's relative responses to diuretic antihypertensives, angiotensin converting enzyme inhibitors and beta-blockers, by determining the presence or absence of a homozygous nucleic acid mutation of A145G, wherein the presence of such homozygous mutation would indicate that there is an increased likelihood that said individual would be more responsive to diuretic antihypertensives than to angiotensin converting enzyme inhibitors and beta-blockers, and (b) selecting an antihypertensive drug according to the result of step (a). In a second embodiment, the method includes predicting an individual's relative responses to diuretic antihypertensives, angiotensin converting enzyme inhibitors and beta-blockers, by determining the presence or absence of a homozygous amino acid substitution of Ser49Gly, or nucleotide variant(s) that make the individual devoid of a beta-1 adrenergic receptor that has a hydroxy group-containing amino acid (e.g., Ser49 or Thr49). The presence of a homozygous Ser49Gly amino acid substitution or the other nucleotide variant(s) would indicate that there is an increased likelihood that said candidate human subject would be more responsive to diuretic antihypertensives than to angiotensin converting enzyme inhibitors and beta-blockers.

In yet another embodiment, the method of treating hypertension comprises: (a) determining the genotype of an individual at the nucleotide 145 position of the beta-1 adrenergic receptor gene; (b) selecting an antihypertensive drug for administration to the individual based on the genotype obtained in said determining step; and (c) administering said drug to the individual or instructing the individual to take said drug. In particular, a thiazide is selected if the individual has a homozygous A145G genotype or a homogenous population of beta-1 adrenergic receptor proteins with a Ser49Gly amino acid variant.

Numerous techniques for detecting genetic variants are known in the art and can all be used for the method of this invention. The techniques can be protein-based or DNA-based. In either case, the techniques used must be sufficiently sensitive so as to accurately detect single nucleotide or amino acid variations. Often, a probe is utilized which is labeled with a detectable marker. Unless otherwise specified in a particular technique described below, any suitable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., *Nucleic Acids Res.*, 14:6115–6128 (1986); Nguyen et al., *Biotechniques*, 13:116–123 (1992); Rigby et al., *J. Mol. Biol.*, 113:237–251 (1977).

In a DNA-based detection method, target DNA sample, i.e., a sample containing the beta-1 adrenergic receptor gene sequence must be obtained from the individual to be tested. Any tissue or cell sample containing the beta-1 adrenergic receptor genomic DNA, mRNA, or cDNA or a portion thereof can be used. For this purpose, a tissue sample containing cell nucleus and thus genome DNA can be obtained from the individual. Blood samples can also be useful except that only white blood cells and other lymphocytes have a cell nucleus, while red blood cells are anucleus and contain mRNA. The tissue or cell samples can be analyzed directly without much processing. Alternatively, nucleic acids including the target gene sequence can be extracted, purified, or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

To determine the presence of a particular genetic variant, one technique is simply sequencing the target gene sequence, particularly the nucleotide sequence region encompassing the genetic variant locus to be detected. Various sequencing techniques are generally known and widely used in the art including the Sanger method and Gilbert chemical method. The newly developed pyrosequencing method monitors DNA synthesis in real time using a luminometric detection system. Pyrosequencing has been shown to be effective in analyzing genetic polymorphisms such as single-nucleotide polymorphisms and thus can also be used in the present invention. See Nordstrom et al., *Biotechnol. Appl. Biochem.*, 31(2):107–112 (2000); Ahmadian et al., *Anal. Biochem.*, 280:103–110 (2000).

Alternatively, the restriction fragment length polymorphism (RFLP) method may also prove to be a useful technique. In particular, if a genetic variation, e.g., if the SNP in the beta-1 adrenergic receptor gene of the present invention results in the elimination or creation of a restriction enzyme recognition site, then digestion of the target DNA with that particular restriction enzyme will generate a different restriction fragment length pattern. Thus, a detected RFLP will indicate the presence of a particular genetic variant.

Another useful approach is the single-stranded conformation polymorphism assay (SSCA), which is based on the altered mobility of a single-stranded target DNA spanning the genetic variant of interest. A single nucleotide change in the target sequence can result in a different intramolecular base pairing pattern, and thus a different secondary structure of the single-stranded DNA, which can be detected in a non-denaturing gel. See Orita et al., *Proc. Natl. Acad. Sci. USA*, 86:2776–2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., *Biotechniques*, 5:1016–24 (1999); Sheffield et al., *Am. J. Hum. Genet.*, 49:699–706 (1991); Wartell et al., *Nucleic Acids Res.*, 18:2699–2705 (1990); and Sheffield et al., *Proc. Natl. Acad. Sci. USA*, 86:232–236 (1989). In addition, the double-strand conformation analysis (DSCA) can also be useful in the present invention. See Arguello et al., *Nat. Genet.*, 18:192–194 (1998).

The presence or absence of the A145G genetic variant in the beta-1 adrenergic receptor gene of an individual can also be detected using the amplification refractory mutation system (ARMS) technique. See e.g., European Patent No. 0,332,435; Newton et al., *Nucleic Acids Res.*, 17:2503–2515 (1989); Fox et al., *Br. J. Cancer*, 77:1267–1274 (1998); Robertson et al., *Eur. Respir. J.*, 12:477–482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., *Clin. Chem.* 43:1336–1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA or mRNA in the presence of labeled dideoxyribonucleotides. A labeled nucleotide is incorporated or linked to the primer only when the dideoxyribonucleotides matches the nucleotide at the SNP locus being detected. Thus, the identity of the nucleotide at the SNP locus can be revealed based on the detection label attached to the incorporated dideoxyribonucleotides. See Syvanen et al., *Genomics*, 8:684–692 (1990); Shumaker et al., *Hum. Mutat.*, 7:346–354 (1996); Chen et al., *Genome Res.*, 10:549–547 (2000).

Another set of techniques useful in the present invention is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., *Science*, 241:1077–1080 (1988); Chen et al, *Genome Res.*, 8:549–556 (1998); Iannone et al., *Cytometry*, 39:131–140 (2000). Thus, for example, to detect the A145G genetic variant in the beta-1 receptor gene, two oligonucleotides can be synthesized, one having the beta-1 adrenergic receptor sequence just 5' upstream from the locus with its 3' end nucleotide being identical to the nucleotide in the mutant locus of the beta-1 adrenergic receptor gene, the other having a nucleotide sequence matching the beta-1 adrenergic receptor sequence immediately 3' downstream from the locus in the beta-1 adrenergic receptor gene. The oligonucleotides can be labeled for the purpose of detection. Upon hybridizing to the target beta-1 adrenergic receptor gene under a stringent condition, the two oligonucleotides are subject to ligation in the presence of a suitable ligase. The ligation of the two oligonucleotides would indicate that the target DNA has a nucleotide variant at the locus being detected.

Detection of small genetic variations can also be accomplished by a variety of hybridization-based approaches. Allele-specific oligonucleotides are most useful. See Conner et al., *Proc. Natl. Acad. Sci. USA*, 80:278–282 (1983); Saiki et al, *Proc. Natl. Acad. Sci. USA*, 86:6230–6234 (1989). Oligonucleotide probes hybridizing specifically to a beta-1 adrenergic receptor gene allele having a particular gene variant at a particular locus but not to other alleles can be designed by methods known in the art. The probes can have a length of, e.g., from 10 to about 50 nucleotide bases. The target beta-1 adrenergic receptor DNA and the oligonucleotide probe can be contacted with each other under conditions sufficiently stringent such that the genetic variant can be distinguished from the wild-type beta-1 adrenergic receptor gene based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular genetic variant (e.g., the A145G genetic variant of the beta-1 adrenergic receptor gene).

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subject to electrophoresis. The mismatched duplexes can be detected based on their electrophoretic mobility that is different from the perfectly matched duplexes. See Cariello, *Human Genetics*, 42:726 (1988). Alternatively, in RNase protection assay, an RNA probe can be prepared spanning the SNP site to be detected and having a detection marker. See Giunta et al., *Diagn. Mol. Path.*, 5:265–270 (1996); Finkelstein et al., *Genomics*, 7:167–172 (1990); Kinszler et al., *Science* 251:1366–1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., *Nucleic Acids Res.*, 25:3377–3378 (1997).

In the mutS assay, a probe can be prepared matching the beta-1 adrenergic receptor gene sequence surrounding the locus at which the presence or absence of the A145G mutation is to be detected, except that a predetermined nucleotide is used at the SNP locus. Upon annealing the probe to the target DNA to form a duplex, the *E. coli* mutS protein is contacted with the duplex. Since the mutS protein binds only to heteroduplex sequences containing a nucleotide mismatch, the binding of the mutS protein will be indicative of the presence of a mutation. See Modrich et al., *Ann. Rev. Genet.*, 25:229–253 (1991).

A great variety of improvements and variations have been developed in the art on the basis of the above-described basic techniques, and can all be useful in detecting the genetic variant of the present invention. For example, the "sunrise probes" or "molecular beacons" utilize the fluorescence resonance energy transfer (FRET) property and give rise to high sensitivity. See Wolf et al., *Proc. Nat. Acad. Sci. USA*, 85:8790–8794 (1988). Typically, a probe spanning the nucleotide locus to be detected are designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., *Nucleic Acids Res.*, 25:2516–2521 (1997); Rychlik et al., *Nucleic Acids Res.*, 17:8543–8551 (1989); Sharkey et al., *Bio/Technology* 12:506–509 (1994); Tyagi et al., *Nat. Biotechnol.*, 14:303–308 (1996); Tyagi et al., *Nat. Biotechnol.*, 16:49–53 (1998). The homo-tag assisted non-dimer system (HANDS) can be used in combination with the molecular beacon methods to suppress primer-dimer accumulation. See Brownie et al., *Nucleic Acids Res.*, 25:3235–3241 (1997).

Dye-labeled oligonucleotide ligation assay is a FRET-based method, which combines the OLA assay and PCR. See Chen et al., *Genome Res.* 8:549–556 (1998). TaqMan is another FRET-based method for detecting SNPs. A TaqMan probe can be oligonucleotides designed to have the nucleotide sequence of the beta-1 adrenergic receptor gene spanning the SNP locus of interest and to differentially hybridize with different beta-1 adrenergic receptor alleles. The two ends of the probe are labeled with a quenching fluorophore and a reporter fluorophore, respectively. The TaqMan probe is incorporated into a PCR reaction for the amplification of a target beta-1 adrenergic receptor gene region containing the locus of interest using Taq polymerase. As Taq polymerase exhibits 5'-3' exonuclease activity but has no 3'-5' exonuclease activity, if the TaqMan probe is annealed to the target beta-1 adrenergic receptor DNA template, the 5'-end of the TaqMan probe will be degraded by Taq polymerase during the PCR reaction thus separating the reporting fluorophore from the quenching fluorophore and releasing fluorescence signals. See Holland et al., *Proc. Natl. Acad. Sci. USA*, 88:7276–7280 (1991); Kalinina et al., *Nucleic Acids Res.*, 25:1999–2004 (1997); Whitcombe et al., *Clin. Chem.*, 44:918–923 (1998).

In addition, the detection in the present invention can also employ a chemiluminescence-based technique. For example, an oligonucleotide probe can be designed to hybridize to either the wild-type or a mutated beta-1 adrenergic receptor gene locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., *Nucleic Acids Res.*, 24:4998–5003 (1996).

The detection of the A145G genetic variant in the beta-1 adrenergic receptor gene sequence in accordance with the present invention can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., *Electrophoresis*, 20:1171–1176 (1999).

Another useful technique that is gaining increased popularity is mass spectrometry. See Graber et al., *Curr. Opin. Biotechnol.*, 9:14–18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucelotides and dideoxyribonucleotides. The resulting mixture of newly extended primers is then analyzed by MALDI-TOF. See e.g., Monforte et al., *Nat. Med.,* 3:360–362 (1997).

In addition, the microchip or microarray technologies are also applicable to the detection method of the present invention. Essentially, in microchips, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., *Biotechniques,* 19:442–447 (1995); Chee et al., *Science,* 274:610–614 (1996); Kozal et al., *Nat. Med.* 2:753–759 (1996); Hacia et al., *Nat. Genet.,* 14:441–447 (1996); Saiki et al., *Proc. Natl. Acad. Sci. USA,* 86:6230–6234 (1989); Gingeras et al., *Genome Res.,* 8:435–448 (1998). Alternatively, the multiple target nucleic acid sequences to be studied are fixed onto a substrate and an array of probes is contacted with the immobilized target sequences. See *Drmanac et al., Nat. Biotechnol.,* 16:54–58 (1998). Numerous microchip technologies have been developed incorporating one or more of the above described techniques for detecting mutations particularly SNPs. The microchip technologies, combined with computerized analysis tools allow fast screening in a large scale. The adaptation of the microchip technologies to the present invention will be apparent to a person of skill in the art apprised of the present disclosure. See, e.g., U.S. Pat. No. 5,925,525 to Fodor et al; Wilgenbus et al., *J. Mol. Med.,* 77:761–786 (1999); Graber et al., *Curr. Opin. Biotechnol.,* 9:14–18 (1998); Hacia et al., *Nat. Genet.,* 14:441–447 (1996); Shoemaker et al., *Nat. Genet.,* 14:450–456 (1996); DeRisi et al., *Nat. Genet.,* 14:457–460 (1996); Chee et al., *Nat. Genet.,* 14:610–614 (1996); Lockhart et al., *Nat. Genet.,* 14:675–680 (1996); Drobyshev et al., *Gene,* 188: 45–52 (1997).

In yet another technique for detecting single nucleotide variations, the Invader® assay utilizes a novel linear signal amplification technology that improves upon the long turn-around times required of the typical PCR DNA sequenced-based analysis. See Cooksey et al., *Antimicrobial Agents and Chemotherapy* 44:1296–1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The Invader® system utilizes two short DNA probes, which are hybridized to a DNA target. The structure formed by the hybridization event is recognized by a special cleavage enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal.

Furthermore, the detection of the A145G genetic variant in the beta-1 adrenergic receptor gene sequence in accordance with the present invention can also be based on Sniper™, a sensitive, high-throughput SNP scoring system designed for the accurate fluorescent detection of specific SNPs from oligonucleotides, PCR fragments or genomic DNA. See Clark and Pickering *Life Science News* 6, 2000, *Amersham Pharmacia Biotech* (2000). Because this method depends on two hybridization events combined with a ligation event, it provides highly accurate allele discrimination. For each SNP, two linear, allele-specific probes are designed that circularize when they anneal to the target sequence. Both allele-specific probes are identical with the exception of the 3'-base, which is varied to complement the polymorphic site. Between the two allele-specific probes is a backbone sequence that encodes binding sites for two rolling circle amplication primers. In the first stage of the assay, target genomic DNA is denatured and then hybridized with a pair of single, allele-specific, open-circle oligonucleotide probes resulting in circularization of the probe. When the 3'-base exactly complements the target DNA, ligation of the probe will preferentially occur. Subsequent detection of the circularized oligonucleotide probes is by rolling circle amplification, whereupon the amplified probe products are detected by fluorescence.

As is apparent from the above survey of the suitable detection techniques, it may or may not be necessary to amplify the target DNA, i.e., the beta-1 adrenergic receptor gene sequence to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both of which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., *Molecular Cloning: A Laboratory Manual,* $2^{nd}$ ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., *J. Clin. Microbiol.,* 34:901–907 (1996); Collins et al., *Nucleic Acids Res.,* 25:2979–2984 (1997); Horn et al., *Nucleic Acids Res.,* 25:4835–4841 (1997); Horn et al., *Nucleic Acids Res.,* 25:4842–4849 (1997); Nilsen et al., *J. Theor. Biol.,* 187: 273–284 (1997).

A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See. Graham et al., *Anal. Chem.,* 69:4703–4707 (1997). The fluorescence correlation spectroscopy is based on the spatio-temporal correlations among fluctuating light signals and trapping single molecules in an electric field. See Eigen et al., *Proc. Natl. Acad. Sci. USA,* 91:5740–5747 (1994). In single-molecule electrophoresis, the electrophoretic velocity of a fluorescently tagged nucleic acid is determined by measuring the time required for the molecule to travel a predetermined distance between two laser beams. See Castro et al., *Anal. Chem.,* 67:3181–3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radio-active isotopes, fluorescence, or other detectable markers. In situ hybridization techniques are well known in the art and their adaptation to the present invention for detecting the presence or absence of the A145G genetic variant in the beta-1 adrenergic receptor gene of a particular individual should be apparent to a skilled artisan apprised of this disclosure.

Protein-based detection techniques may also prove to be useful, especially in detecting the Ser49Gly amino acid substitution of the present invention. To detect amino acid variations, protein sequencing techniques may be used. For example, a beta-1 adrenergic receptor protein or fragment thereof can be synthesized by recombinant expression using a beta-1 adrenergic receptor DNA fragment isolated from an individual to be tested. Preferably, a beta-1 adrenergic receptor cDNA fragment of no more than 100 to 150 base pairs encompassing the polymorphic locus to be determined is used. The amino acid sequence of the peptide can then be determined by conventional protein sequencing methods. Alternatively, the recently developed HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., *Anal. Chem.*, 72:757–763 (2000).

Other useful protein-based detection techniques include immunoaffinity assays based on idiotype-specific antibodies, i.e., antibodies specific to mutant beta-1 adrenergic receptor proteins according to the present invention. The method for producing such antibodies is described above in detail. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well known antibody-based techniques can also be used including, e.g., enzyme-linked immunosorbent assay (ELISA), radioimmuno-assay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

Thus, various techniques can be used in genotyping the human beta-1 adrenergic receptor gene of an individual to determine, in the individual, the presence or absence of the A145G genetic variant or the Ser49Gly amino acid variant. Typically, once the presence or absence of the nucleotide or amino acid variant of the present invention is determined, the result can be cast in a transmittable form that can be communicated to others (including the patient). Such a form can vary and can be tangible or intangible. The result with regard to the presence or absence of a beta-1 adrenergic receptor genetic variant of the present invention in the individual tested can be embodied in descriptive statements, diagrams, photographs, charts, images or any other visual forms. For example, images of gel electrophoresis of PCR products can be used in explaining the results. Diagrams showing where a genetic variant occurs in an individual's beta-1 adrenergic receptor gene are also useful in indicating the testing results. The statements and visual forms can be recorded on a tangible media such as papers, computer readable media such as floppy disks, compact disks, etc., or on an intangible media, e.g., an electronic media in the form of email or website on the Internet or an intranet. In addition, the result with regard to the presence or absence of a beta-1 adrenergic receptor genetic variant of the present invention in the individual tested can also be recorded in a sound form and transmitted through any suitable media, e.g., analog or digital cable lines, fiber optic cables, etc., via telephone, facsimile, wireless mobile phone, internet phone and the like.

The present invention also provides a kit for predicting, in an individual, effective response to one of three classes of antihypertensive drugs. The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit also includes various components useful in detecting nucleotide or amino acid variants discovered in accordance with the present invention using the above-discussed detection techniques.

In one preferred embodiment, the detection kit includes one or more oligonucleotides useful in detecting the A145G genetic variant in the beta-1 adrenergic receptor gene sequence. Preferably, the oligonucleotides are designed such that they hybridize only to a beta-1 adrenergic receptor gene sequence containing the particular A145G genetic variant discovered in accordance with the present invention, under stringent conditions. Thus, the oligonucleotides can be used in mutation-detecting techniques such as allele-specific oligonucleotides (ASO), allele-specific PCR, TaqMan, chemiluminescence-based techniques, molecular beacons, and improvements or derivatives thereof, e.g., microchip technologies. The oligonucleotides in this embodiment preferably have a nucleotide sequence that matches a nucleotide sequence of the mutant beta-1 adrenergic receptor gene allele containing the A145G genetic variant to be detected. The nucleotide variant preferably is not located at the 5' or 3' end, but in other positions in the oglionucleotides. The length of the oligonucleotides in accordance with this embodiment of the invention can vary depending on its nucleotide sequence and the hybridization conditions employed in the detection procedure. Preferably, the oligonucleotides contain from about 10 nucleotides to about 100 nucleotides, more preferably from about 15 to about 75 nucleotides. Under certain conditions, a length of 18 to 30 may be optimum. In any event, the oligonucleotides should be designed such that it can be used in distinguishing one genetic variant from another at a particular locus under predetermined stringent hybridization conditions. The hybridization of an oligonucleotide with a nucleic acid and the optimization of the length and hybridization conditions should be apparent to a person of skill in the art. See generally, Sambrook et al., *Molecular Cloning: A Laboratory Manual*, $2^{nd}$ ed., Cold Spring Harbor Laboratory, Cold Spring Harbor, N.Y., 1989. Notably, the oligonucleotildes in accordance with this embodiment are also useful in mismatch-based detection techniques described above, such as electrophoretic mobility shift assay, RNase protection assay, mutS assay, etc.

In another embodiment of this invention, the kit includes one or more oligonucleotides suitable for use in detecting techniques such as ARMS, oligonucleotide ligation assay (OLA), and the like. The oligonucleotides in this embodiment include a beta-1 adrenergic receptor gene sequence immediately 5' upstream from the A145G genetic variant to be analyzed. The 3' end nucleotide is a nucleotide variant in accordance with this invention.

The oligonucleotides in the detection kit can be labeled with any suitable detection marker including but not limited to, radioactive isotopes, fluorephores, biotin, enzymes (e.g., alkaline phosphatase), enzyme substrates, ligands and antibodies, etc. See Jablonski et al., *Nucleic Acids Res.*, 14:6115–6128 (1986); Nguyen et al., *Biotechniques*, 13:116–123 (1992); Rigby et al., *J. Mol. Biol.*, 113:237–251 (1977). Alternatively, the oligonucleotides included in the kit are not labeled, and instead, one or more markers are provided in the kit so that users may label the oligonucleotides at the time of use.

In another embodiment of the invention, the detection kit contains one or more idiotype-specific antibodies, i.e., antibodies only recognize certain beta-1 adrenergic receptor proteins or polypeptides containing the A145G nucleotide variant of the present invention. Methods for producing and using such antibodies have been described above in detailed.

Various other components useful in the detection techniques may also be included in the detection kit of this invention. Examples of such components include, but are not limited to, Taq polymerase, deoxyribonucleotides, dideoxyribonucleotides other primers suitable for the amplification of a target DNA sequence, RNase A, mutS protein, and the like. In addition, the detection kit preferably includes instructions on using the kit for detecting the A145G genetic variant of the beta-1 adrenergic receptor gene sequences.

In one embodiment of the present invention, the method is primarily based on binding affinities to screen for compounds capable of interacting with or binding to a beta-1 adrenergic receptor protein containing one or more amino acid variants. Compounds to be screened may be peptides or derivatives or mimetics thereof, or non-peptide small molecules. Conveniently, commercially available combinatorial libraries of compounds or phage display libraries displaying random peptides are used.

EXAMPLE

For our study, three drugs—fosinopril, atenolol, and hydrochlorothiazide—were administered to patients with symptoms diagnosed as hypertension (a diastolic blood pressure above 89 mmHg and a systolic blood pressure above 139 mmHg). Since essential hypertension is a complex multifactorial disease with an environmental component and a genetic interaction basis, we selected a homozygous patient sample from Sardinia, which ensured genetic homogeneity. Piazza, *Science* 260:1767–9 (1993). Patients were unrelated Sardinian from at least 2 generations. Approximately 75% of the patients were previously untreated for hypertension, whereas the remaining were absent from antihypertensive treatment for at least 6 months prior to testing, thus ensuring that modifications in blood pressure during the study were mostly due to the drug under study and not the spurious effects related to previous treatments.

After a 2-month pre-treatment period, during which blood pressure was measured periodically, patients with blood pressure (as average of 3 measurements performed in standard conditions) still over 140/90 (n=494) where randomly assigned to one of the following drugs: atenolol 100 mg b.i.d., hydrochlorothiazide (HCTZ) 25 mg u.i.d. or fosinopril 20 mg u.i.d. for 2 months. After a treatment was begun, patient blood pressure, heart rate and body weight were assessed every 2 weeks, and values at +4 and +8 weeks tabulated and considered for analysis.

Genomic DNA was extracted from the leukocytes of each individual using a genomic DNA extraction kit based on chloroform precipitation/ethanol extraction. Genomic DNA of the beta-1 adrenergic receptor gene was then amplified using standard PCR procedures. The PCR product was diluted 1:10 in EDTA 1 mM and then submitted for automated sequencing carried out with an Applied Biosystems Sequencer using dye primer chemistry. Each individual was then assigned a genotype based on the results of sequencing the PCR product of the beta-1 adrenergic receptor gene containing the locus associated with the variant allele of the present invention.

A case-control study was conducted with normotensives and hypertensive unrelated Sardinians. Normotensives had a blood pressure of less than 140/85 and were over 60 of age. After excluding individuals with missing phenotypic data or genotype, the final number of cases and controls was 516 and 180, respectively. The characteristics of cases and controls (age, blood pressure, BMI) were deliberately different due to selection criteria (Table 1). For both normotensive and hypertensive groups the Hardy-Weinberg equilibrium was respected.

TABLE 1

Baseline Characteristics Of Hypertensives And Normotensives

|  | Hypertensives | Normotensives |
|---|---|---|
| Number | 516 | 180 |
| Sex (M, %) | 342(58.9%) | (81, 45%) |
| Age | 47.8 ± 9.8 | 65.8 ± 8.9 |
| BMJ (Kg/m$^2$) | 27.1 ± 3.9 | 26.2 ± 4.5 |
| bSBP (mmHg) | 158.1 ± 15.5 | 125 ± 8 |
| bDBP (mmHg) | 105.2 ± 8.0 | 77 ± 4 |
| bMBP (mmHg) | 122.8 ± 9.5 | 92 ± 3 |

To evaluate the association between each patient's genotype and the response of the individual to the respective drug, the change in blood pressure was analyzed from the baseline to the follow-up measurements at 4 and 8 weeks. A linear regression model was then used to adjust for the effect of baseline blood pressure levels and sex of the individual. The difference in average change of blood pressure between genotypes for each time interval was determined through analysis of covariance. When stratified for the genotype, individuals homozygous for the A145G nucleotide variant of the present invention were more likely (p=0.0055) to experience a significant decrease in blood pressure when treated with hydrochlorothiazide than fosinopril and atenolol. Table 2 below demonstrates the beta-1 adrenergic receptor genotypes as they were distributed among the patients of the study. The average change in blood pressure (mmHg) for the three treatment groups, each according to the genotype is shown in Table 3.

TABLE 2

Beta-1 Adrenergic Receptor Genotype Distribution According to Treatment

|  | Fosinopril | Atenolol | Hydrochlorothiazie | Total |
|---|---|---|---|---|
| Homozygous Wild-Type (AA) | 115 | 210 | 139 | 464 |
| Heterozygous (AG) | 24 | 52 | 31 | 107 |
| Homozygous Genetic Variant (GG) | 3 | 5 | 2 | 10 |

TABLE 3

Average Change in Blood Pressure for the Three Treatment Groups

|    | All Groups | Fosinopril | Atenolol | Hydrochlorothiazide |
|----|------------|------------|----------|---------------------|
| AA | −13.9      | −12.3      | −17.3    | −10.2               |
| AG | −14.4      | −8.6       | −17.9    | −12.9               |
| GG | −18.3      | −23.0      | −10.6    | −30.5               |

The data presented herein shows that the relative benefit of the three different classes of antihypertensive drugs depends on the genotype at the 145 nucleotide position of beta-1 adrenergic receptor gene. Specifically, thiazides are more effective than beta-blockers in individuals with a homozygous A145G genotype, but less effective in individuals with a homozygous A145A genotype. The treatment with an angiotensin converting enzyme inhibitor showed similar, but less pronounced, trends as the thiazide treatment. In both the thiazide and angiotensin converting enzyme inhibitors treatment groups, individuals with the homozygous A145G genotype are most responsive to treatment.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for selecting an antihypertensive treatment for an individual, comprising:
   determining the genotype of an individual at the nucleotide 145 position of the beta-1 adrenergic receptor gene, wherein the presence of a homozygous A145G genetic variant would indicate an increased likelihood that said individual will respond more favorably to hydrochlorothiazide than to fosinopril or atenolol; and
   selecting hydrochlorothiazide as the antihypertensive treatment for said individual if said individual is homozygous for said A145G genetic variant.

2. A method of treating hypertension comprising:
   determining the genotype of an individual at the nucleotide 145 position of the beta-1 adrenergic receptor gene;
   selecting an antihypertensive drug from the group consisting of hydrochlorothiazide, atenolol, and fosinopril for administration to the individual based on the genotype obtained in said determining step, wherein a hydrochlorothiazide is selected if said individual has a homozygous A145G genotype; and
   administering said drug to said individual or instructing the individual to take said drug.

3. A method for predicting the relative responses of an individual to different antihypertensive drugs, said method comprising:
   assaying a tissue sample from an individual with hypertension to determine the presence or absence of an A145G nucleotide variant or a nucleotide variant resulting in a Ser49Gly amino acid substitution in a nucleic acid of said individual encoding beta-1 adrenergic receptor, wherein the presence of a homozygous A145G genetic variant or a homozygous genetic variant resulting in the Ser49Gly amino acid variant would indicate an increased likelihood that said individual will respond more favorably to hydrochlorothiazide than to fosinopril or atenolol.

4. The method of claim 3, wherein said assaying step comprises analyzing nucleic acids isolated from said individual.

5. The method of claim 3, wherein said assaying step comprises performing mass spectrometry analysis on beta-1 adrenergic receptor nucleic acids obtained from said individual.

6. The method of claim 3, wherein said assaying step comprises rolling circle amplification of a portion of a beta-1 adrenergic receptor nucleic acid obtained from said individual.

7. The method of claim 3, wherein said assaying step comprises performing Invader assay on a beta-1 adrenergic receptor nucleic acid obtained from said individual.

8. The method of claim 3, wherein said assaying step comprises sequencing beta-1 adrenergic receptor nucleic acids obtained from said individual.

9. The method of claim 3, wherein said assaying step comprises hybridization with an allele specific probe.

10. A method for predicting the relative responses of an individual to different drugs, said method comprising:
    assaying a tissue sample from an individual with hypertension to determine the genotype at the nucleotide 145 position of the beta-1 adrenergic receptor gene, wherein the presence of a homozygous A145G genetic variant or a homozygous genetic variant resulting in the Ser49Gly amino acid variant would indicate an increased likelihood that said individual will respond more favorably to hydrochlorothiazide than to fosinopril and or atenolol.

11. A method for selecting candidate human subjects for participation in a clinical trial involving an antihypertensive drug, comprising:

determining the genotype of an individual at the nucleotide 145 position of the beta-1 adrenergic receptor gene, wherein the presence of a homozygous A145G genetic variant would indicate an increased likelihood that said individual will respond more favorably to hydrochlorothiazide than to fosinopril and or atenolol; and deciding whether to include said individual in the clinical trial based on the result of the determining step.

12. A method for predicting the relative responses of an individual to different drugs, said method comprising:

manufacturing a transmittable form of information by assaying a tissue sample from an individual with hypertension to determine the genotype at the nucleotide 145 position of the beta-1 adrenergic receptor gene; and embodying the genotype obtained in said assaying step in a transmittable form, wherein the presence of a homozygous A 145G genetic variant would indicate an increased liklihood that said individual will respond more favorably to hydrochlorthiazide than to fosinopril atenolol.

* * * * *

UNITED STATES PATENT AND TRADEMARK OFFICE
CERTIFICATE OF CORRECTION

PATENT NO. : 7,195,873 B2  Page 1 of 1
APPLICATION NO. : 10/331192
DATED : March 27, 2007
INVENTOR(S) : Filigheddu et al.

It is certified that error appears in the above-identified patent and that said Letters Patent is hereby corrected as shown below:

Col. 19 Claim 2, Line 54, please delete "a".

Col. 21 Claim 10, Line 3, please delete "and".

Col. 21 Claim 11, Line 12, please delete "and".

Col. 22 Claim 12, Line 11, please change "hydrochlorthiazide" to --hydrochlorothiazide--.

Signed and Sealed this

Nineteenth Day of June, 2007

JON W. DUDAS
*Director of the United States Patent and Trademark Office*